United States Patent
Barber et al.

[11] Patent Number: 5,773,713
[45] Date of Patent: Jun. 30, 1998

[54] ENVIRONMENTAL MONITORING OF ORGANIC COMPOUNDS

[75] Inventors: Christopher Barber, Darlington; Bradley Mark Patterson, Sorrento; Gregory Bruce Davis, Floreat; Terence Robert Power, Mullaloo, all of Australia

[73] Assignee: CRC For Waste Management & Pollution Control Limited, Australia

[21] Appl. No.: 619,537

[22] PCT Filed: Jul. 26, 1995

[86] PCT No.: PCT/AU95/00456

§ 371 Date: Feb. 10, 1997

§ 102(e) Date: Feb. 10, 1997

[87] PCT Pub. No.: WO96/03633

PCT Pub. Date: Feb. 8, 1996

[30] Foreign Application Priority Data

Jul. 26, 1994 [AU] Australia ................. PM7074

[51] Int. Cl.⁶ ............ G01N 13/05; G01N 1/00; B01D 15/08
[52] U.S. Cl. ............ 73/61.41; 73/61.41; 73/61.59; 73/19.1; 210/544; 210/651; 422/83; 422/256
[58] Field of Search ............ 73/61.41, 61.53, 73/61.77, 61.73, 61.59, 61.47, 19.1, 19.12, 864.81; 210/175, 634, 644, 649, 321.75–327.87, 321.74; 422/68.1, 83, 256, 260

[56] References Cited

U.S. PATENT DOCUMENTS

| | | | |
|---|---|---|---|
| 3,438,241 | 4/1969 | McKinley | 73/23 |
| 3,619,986 | 11/1971 | Mormont et al. | 55/158 |
| 3,624,710 | 11/1971 | Carter et al. | 73/61.1 R |
| 3,926,561 | 12/1975 | Lucero | 23/232 R |
| 4,201,550 | 5/1980 | Noszticzius et al. | 23/232 E |
| 4,357,824 | 11/1982 | Foss et al. | 73/19 |
| 4,409,819 | 10/1983 | Smolin | 73/61.1 R |
| 4,541,268 | 9/1985 | Odernheimer | 73/23 |
| 4,715,217 | 12/1987 | Coyne et al. | 73/61.1 C |
| 4,860,577 | 8/1989 | Patterson | 73/64.3 |
| 4,958,529 | 9/1990 | Vestal | 73/864.81 |
| 5,005,403 | 4/1991 | Steudle et al. | 73/64.3 |
| 5,131,266 | 7/1992 | Hassett | 73/61.41 R |
| 5,472,613 | 12/1995 | Schofield | 210/634 |
| 5,492,838 | 2/1996 | Pawliszyn | 436/178 |
| 5,605,664 | 2/1997 | Lauks et al. | 422/83 |

FOREIGN PATENT DOCUMENTS

| | | |
|---|---|---|
| 0 326 995 | 8/1989 | European Pat. Off. |
| 1 317 912 | 5/1973 | United Kingdom . |
| WO95/14223 | 5/1995 | WIPO . |

*Primary Examiner*—Hezron E. Williams
*Assistant Examiner*—J. David Wiggins
*Attorney, Agent, or Firm*—Kelly Bauersfeld Lowry & Kelley, LLP

[57] ABSTRACT

Environmental monitoring of low concentration of organic compounds in a medium such as ground water or another environmental fluid is effected by using a diffusion cell (112) having a polymeric membrane formed into a helical tube (125) and immersed in the environmental fluid so that organic compounds at ppb and ppt concentrations diffuse into and through the polymeric material. A carrier gas in the polymeric tube acquires a concentration of the organic compounds substantially in equilibrium with the concentration of the organic compounds in the environmental fluid. For the purpose of permitting monitoring with detectors (116) which are not sensitive to extremely low levels of organic compounds, a concentrating device such as a thermal desorption tube (114) can be provided for processing the gas and periodic thermal activation to discharge therefrom organic compounds to be detected at a sensor.

19 Claims, 7 Drawing Sheets

ENVIRONMENTAL MONITORING OF ORGANIC COMPOUNDS

The present invention relates to a method and apparatus for environmental monitoring of low concentration levels of organic compounds, and relates particularly, though not exclusively, to a method and apparatus for real-time monitoring of low concentration levels of volatile organic compounds (VOCs) in groundwater from an aquifer in situ using a diffusion cell.

Where drinking water is obtained underground from an aquifer, it is essential that the water be carefully monitored for contaminants. Contaminants of particular concern are VOCs which include such organic compounds as benzene, toluene, ethylbenzene, xylene (BTEX compounds), trichloroethene (TCE), halomethanes and other derivatives thereof. One of the potential sources of VOCs in groundwater is leakage of organic solvents and petroleum fuels for example from underground tanks which may be susceptible to leaking. Contamination of ground water with VOCs in such locations may occur and can be difficult to detect.

Recommended concentration levels of VOCs in drinking water are usually extremely low. The VOCs need, therefore, to be detected relatively accurately at low concentration levels, typically in the parts per trillion (ppt) to parts per billion (ppb) range. In many places permitted concentrations have been progressively lowered. Measurement of VOCs at such low levels may also be necessary in atmospheric monitoring. Monitoring of VOCs is often required on a continuous or semi-continuous basis to provide real-time data on the level of contamination in the environment.

A diffusion cell consists of a sealed hollow membrane containing a gas phase connected directly to a gas sensing device. The membrane, which is permeable to gases such as oxygen and volatile organic compounds but relatively impermeable to water, provides an interface between the gas phase within the cell and the medium external to the cell. A diffusion cell relies on establishment of an equilibrium between the atmosphere within the open volume and the medium external to the cell.

Diffusion cells constructed of various polymeric materials are known to absorb organic or other compounds and have been used, for example, to determine dissolved methane and dissolved oxygen concentrations in groundwater. Silicone materials, for example, preferentially allow organic compounds to permeate therethrough while rejecting water and other highly polar molecules. Steady state diffusion across a polymeric material of a diffusion cell is driven by partial pressures of the liquid and gas phase each side of the polymeric material, respectively. This diffusion at steady state can be defined by Fick's first law of diffusion.

A known monitoring apparatus comprises a polymeric diffusion cell connected on each end thereof to an upstream and downstream tube, respectively. These tubes are referred to as access lines. The access lines are usually constructed of stainless steel or other materials which are relatively impermeable to VOCs such as nylon. The diffusion cell usually comprises an elongate tube, for example constructed of silicone. The access lines and diffusion cell are purged with a carrier liquid or carrier gas, such as air. Samples of gas are taken from the downstream access line for determination of gas concentration, such as methane, using a gas chromatograph. A problem with this technique is that the detector is relatively expensive and not portable. Furthermore, gas concentrations of non-halogenated VOC's cannot be measured in the ppb range.

Another known monitoring apparatus, using a compact solid state detector for measuring selected compounds such as chlorinated hydrocarbons, has been used to provide real-time continuous analysis of such compounds. A sensor used in the monitoring apparatus comprises a permeable silicone tube in fluid communication with access lines through which a flow of carrier gas is provided. The solid state detector is connected to the downstream access line. The carrier gas flows through the access lines and the permeable silicone tube at a relatively high flow rate, for example, 170 milliliters per minute (ml min$^{-1}$). The sensitivity of this monitoring apparatus is also limited to the parts per million (ppm) range.

At least preferred embodiments of the present invention are aimed at providing a method and apparatus for environmental monitoring of low concentration levels of organic compounds, for example in the parts per billion (ppb) range, relatively accurately. Furthermore, it is desirable to provide an apparatus which can be used in situ for real-time monitoring of such low levels of organic compounds yet the apparatus should be relatively simple, efficient, cost-effective, and accurate to use.

According to one aspect of the present invention, there is provided a method of environmental monitoring of low concentration levels of organic compounds in an environmental medium, the method comprising the steps of:

locating a diffusion cell in the environmental medium for sampling the organic compounds, the diffusion cell including a polymeric membrane into which and through which the organic compounds diffuse, the polymeric membrane providing partitioning between the environmental medium and a zone for a carrier fluid, providing the diffusion cell with a carrier fluid such that the carrier fluid acquires a concentration of the organic compounds substantially in equilibrium with the concentration of the organic compounds in the environmental medium whereby, in use, low concentration levels of the organic compounds in the environmental medium can be detected in a manner which has a relatively high degree of sensitivity, monitoring the organic compounds in the carrier fluid, and providing an output signal representative of the organic compounds in the environmental medium.

Important embodiments are those in which real time monitoring occurs.

Advantageously the predetermined flow rate of the carrier fluid is selected so that an equilibrium constant for each organic compound can be used to calculate low concentration levels of each of the organic compounds in the environmental medium relatively accurately.

Preferably the equilibrium constant is defined as Henry's law coefficient for each of the organic compounds.

Advantageously the predetermined flow rate of the carrier fluid can be determined by calibration of a mathematical model based on experimental data.

Preferably the experimental data is based on one or more test variables including: the diffusion cell geometry, material of construction of the diffusion cell, and the composition of the organic compounds.

Advantageously the predetermined flow rate of the carrier fluid can be varied to substantially minimise any detrimental response characteristics resulting from partitioning of the organic compounds absorbed within the diffusion cell.

In an important embodiment the carrier fluid has a flow rate of less than 10 ml/min and preferably 2–5 ml/min, although much lower flow rates may be possible.

Typically one of the detrimental effects includes a memory effect wherein a first organic compound absorbed in high concentrations within the diffusion cell relative to the environmental medium may be detected inaccurately relative to a second organic compound absorbed in low concentrations within the diffusion cell relative to the environmental medium, when the concentration of such compounds changes with time. For example, trimethylbenzene has a higher degree of partitioning than benzene. Thus, as the concentration of organic compounds changes in the environmental medium, those organic compounds which have a higher degree of partitioning cause significant delay for the organic compounds to equilibrate across the diffusion cell. This delay response time is known as the "memory effect" and account of this should be taken in interpreting results. For known organic compounds calibration and correction for this effect is appropriate to improve real time monitoring.

Typically the method further comprises the step of detecting the presence of the organic compounds in the carrier fluid.

Preferably the method further comprises the step of concentrating the organic compounds before said step of detecting.

Preferably the step of detecting the presence of the organic compounds in the carrier fluid can be performed using a compact solid state detector which is relatively sensitive.

Examples of organic compounds for which monitoring can occur are BTEX (benzene, toluene, ethylbenzene, xylene), bromoform, trichloroethene (TCE) and methane.

According to a further aspect of the present invention there is provided an apparatus for use in situ for real-time monitoring of low concentration levels of organic compounds in an environmental medium, the apparatus comprising:

a diffusion cell for sampling the organic compounds in the environmental medium by diffusion;

a concentrating means in fluid communication with the diffusion cell for concentrating the sampled organic compounds; and, a detector in fluid communication with the concentrating means for detecting the presence of the organic compounds whereby, in use, low concentration levels of the organic compounds in the environmental medium can be detected relatively accurately.

Preferably the apparatus further comprises fluid flow generating means coupled to the diffusion cell for generating a predetermined flow rate of a carrier fluid to the diffusion cell and delivering the carrier fluid to the concentrating means, wherein the predetermined flow rate of the carrier fluid is controlled to be sufficiently low so that the concentration of the organic compounds in the diffusion cell is substantially in equilibrium with the concentration of the organic compounds in the environmental medium.

Preferably the diffusion cell is tubular and constructed of a silicone material.

Preferably the concentrating means comprises a thermal desorption tube having an absorbent material for absorbing the sampled organic compounds and a device such as an oven for desorbing the sampled organic compounds absorbed within said material.

Advantageously the detector comprises a compact solid state detector that can be used for providing real-time analysis of preselected organic compounds.

In order to achieve a better understanding of the nature of the present invention possible embodiments will now be described, by way of example only, with reference to the accompanying drawings in which.

For the purpose of the following description the concentration unit nanograms per liter (ng $1^{-1}$), or an equivalent thereof, is considered to be the same as concentration levels of ppt.

Figure 1:
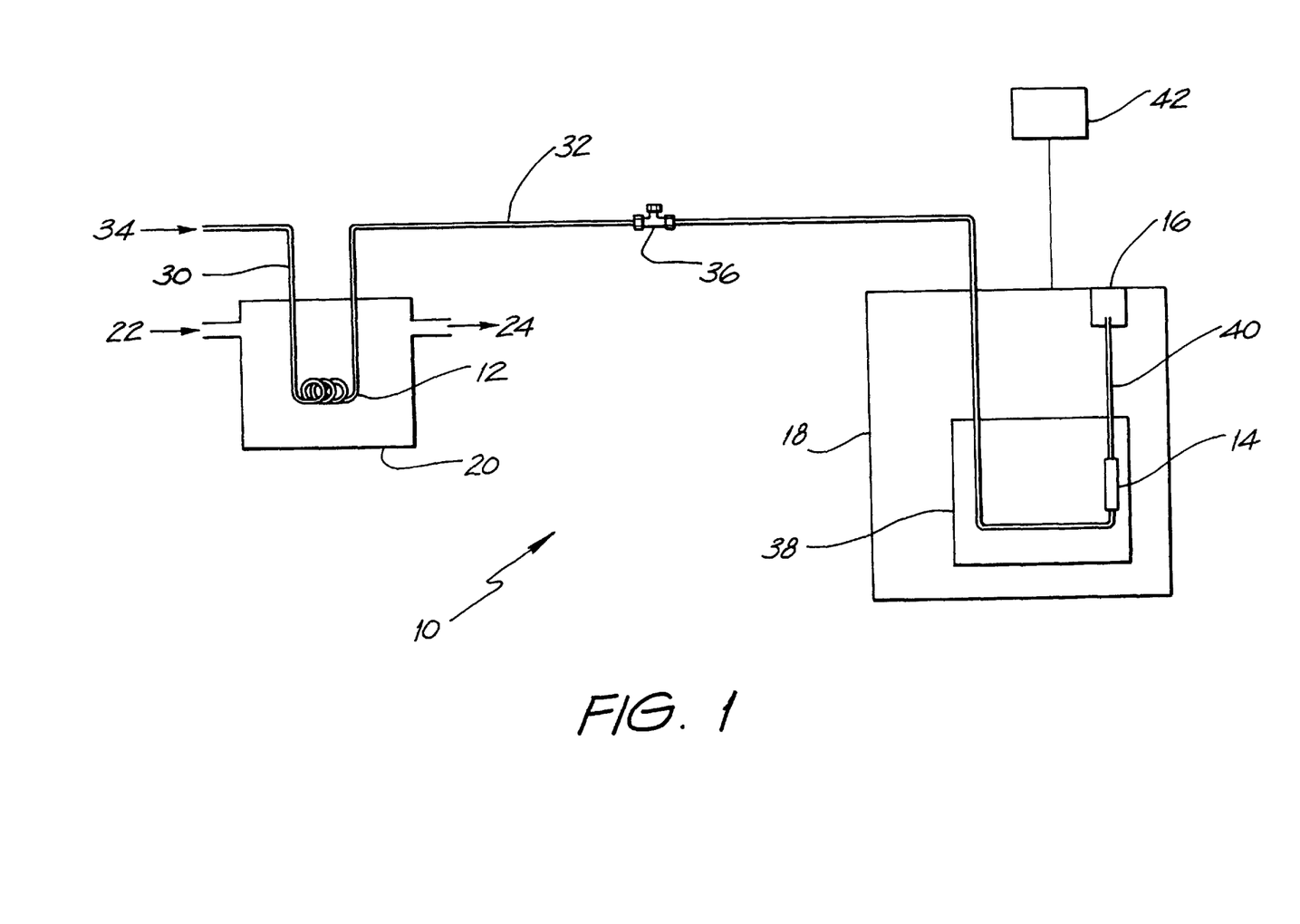
FIG. 1 is a schematic of one embodiment of an apparatus of the present invention and illustrates laboratory test equipment.
Figure 6:
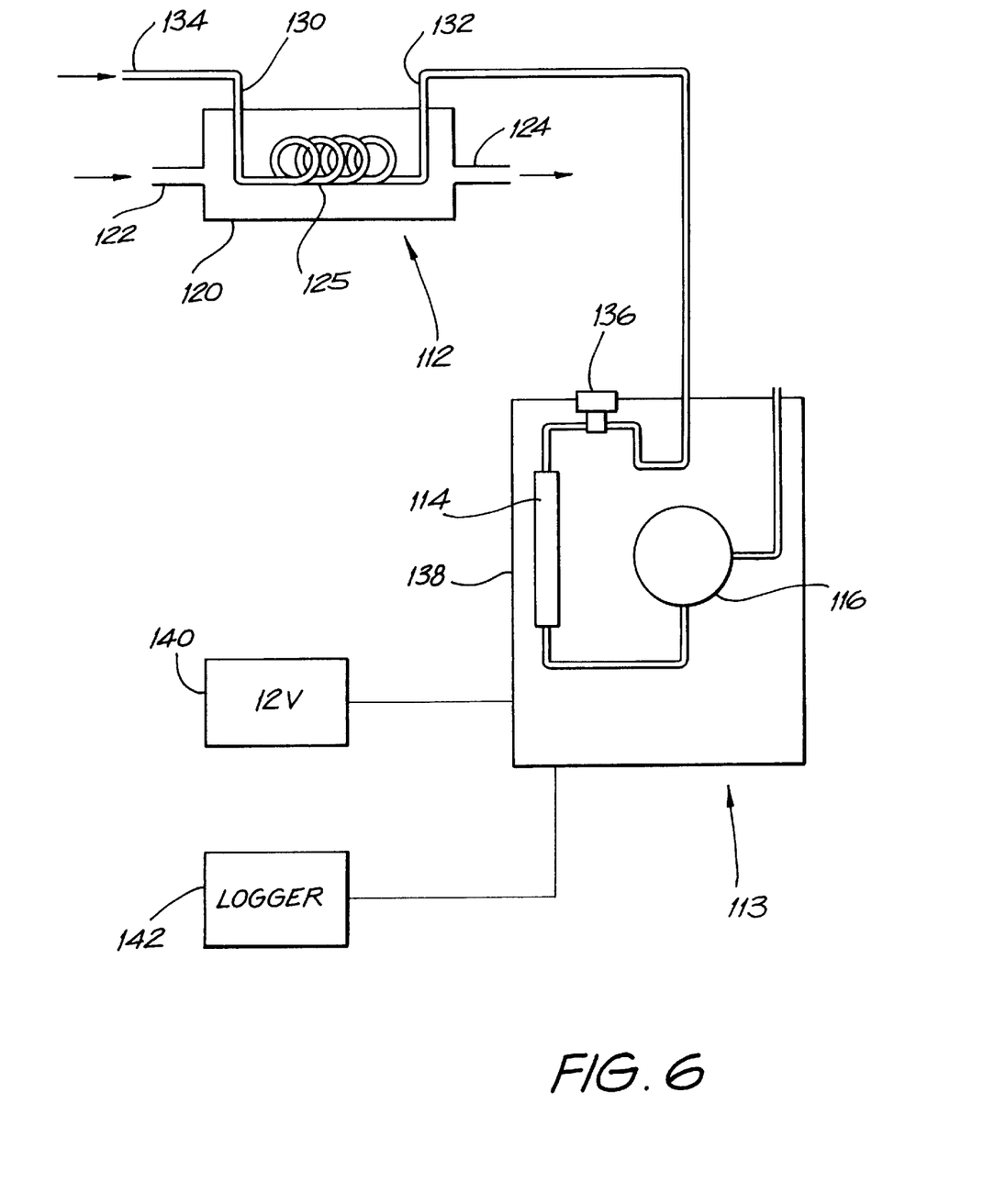
FIG. 6 illustrates a second embodiment being a schematic of a prototype for use in situ for real time monitoring.

The embodiment of FIG. 1 is a schematic of laboratory test equipment (on the basis of which a prototype shown in FIG. 6 has been developed for use in situ for real-time environmental monitoring in the field such as, for example, for the monitoring of VOCs in groundwater). The embodiment now described with reference to FIG. 1 is merely illustrative of the field application of the present invention.

The apparatus comprises a diffusion cell 12 connected to a detection unit 18 and arranged to monitor organic compounds in water, which is supplied to a stainless steel flow cell 20 through an inlet 22, water being discharged through outlet 24. The diffusion cell 12 comprises a tube of silicone material formed into a helical coil. The tube has an inside diameter of 1 mm, an outside diameter of 1.5 mm and a total length of 1 m. The helical coil is connected to an upstream access line 30 having an inlet 34 through which carrier fluid (in this case high purity nitrogen) is inserted. The coil is also connected to a downstream access line 32, which conveys the carrier fluid into an oven 38 in which is located a carbotrap thermal desorption tube 14. Downstream from this thermal desorption tube 14 is a discharge access line 40 for discharging the carrier fluid to an electron capture detector (ECD) 16. The apparatus further comprises an integrator 42 electrically connected to the ECD 16 for recording signals from the ECD 16 and corresponding to concentrations of organic compounds.

The apparatus further includes an injection port 36 in the line 32, which is used to calibrate the apparatus by injecting known amounts of a known standard organic compound into the injection port 36.

Figure 2:
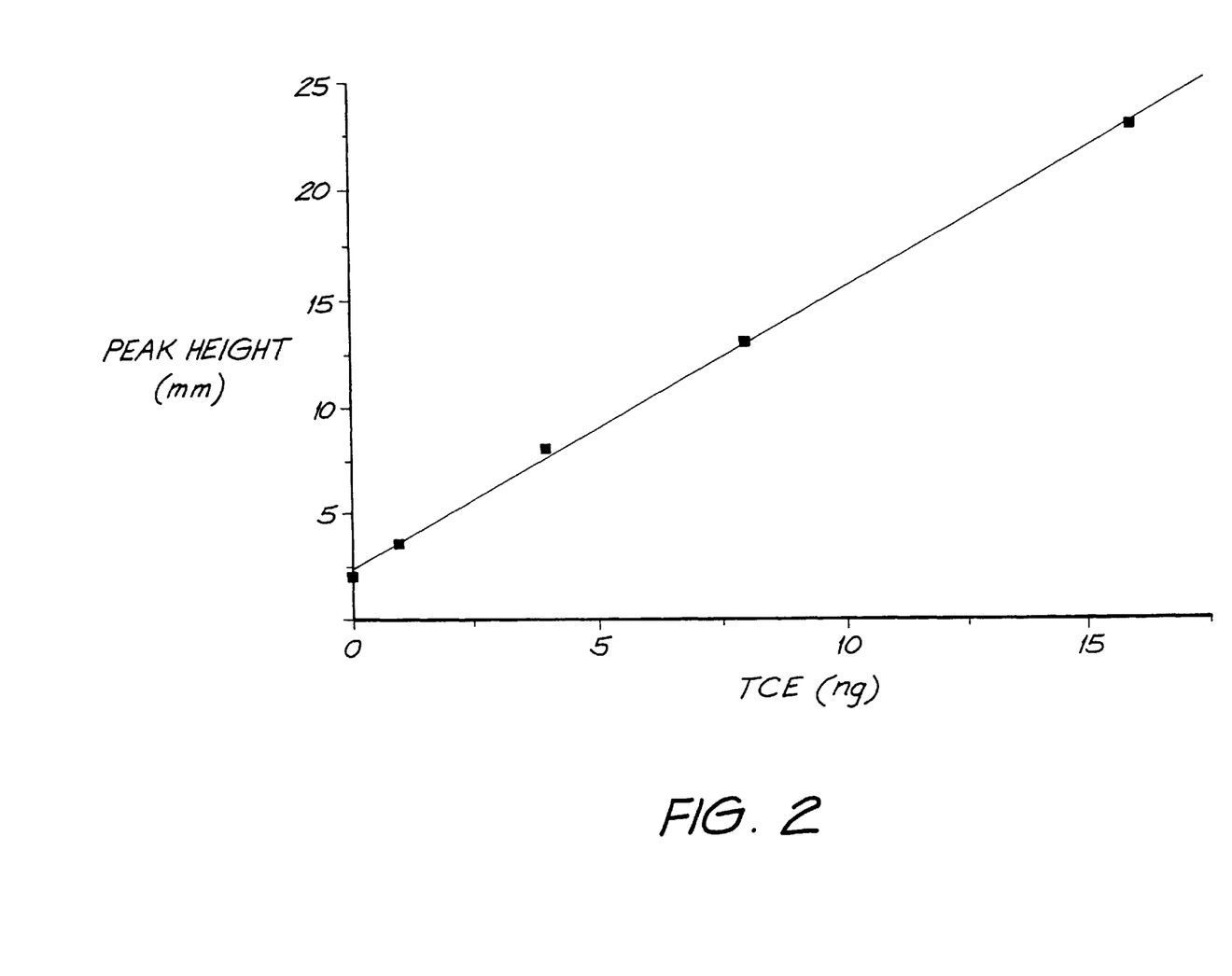
FIG. 2 is a graph of a range of known low amounts of trichloroethene (TCE) and a corresponding peak reading from an electron capture detector (ECD) used in the apparatus of FIG. 1.

For example known amounts of TCE and bromoform have been injected and a peak reading from the ECD 16 was then plotted against the known amount of each standard compound. FIG. 2 is a graph of injected amounts of TCE and the corresponding peak reading from the ECD 16. A collection period of one hour is used with a carrier fluid, in this case pure nitrogen 23 at a flow rate of 5 milliliters per minute (ml min$^{-1}$). TCE is detectable from the ECD 16 down to an injected mass of 4 ng of TCE. Below 4 ng of TCE, background noise on the ECD 16 output is relatively indistinguishable from a peak reading for TCE based on a signal to noise ratio of 3 to 1. This is considered, therefore, to be the sensitivity of the ECD 16. 4 ng of TCE corresponds to a gas concentration of 13 ng $1^{-1}$ and, based on a Henry's law constant of 0.36, corresponds to an aqueous concentration detection limit of approximately 37 ng 1–1.

When the ECD 16 is calibrated with bromoform, the detection limit is 36 ng or approximately nine times less than TCE. 36 ng of bromoform corresponds to a gas concentration of 120 ng $1^{-1}$ and based on a Henry's law constant of 0.024 corresponds to an aqueous concentration detection limit of approximately 5000 ng $1^{-1}$.

Figure 3:
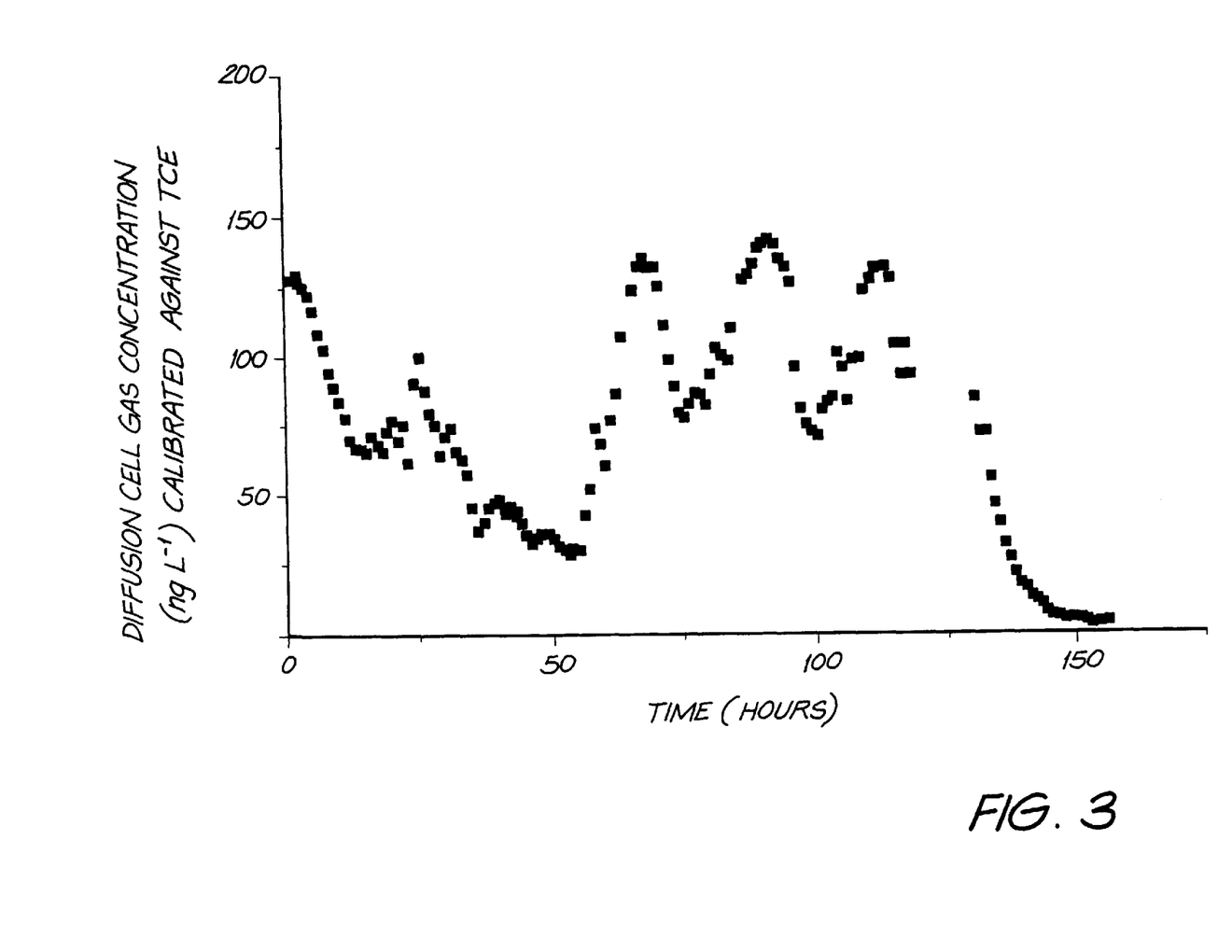
FIG. 3 is a graph showing relative concentrations of halomethanes obtained from the apparatus of FIG. 1 calibrated against TCE.
Figure 4:
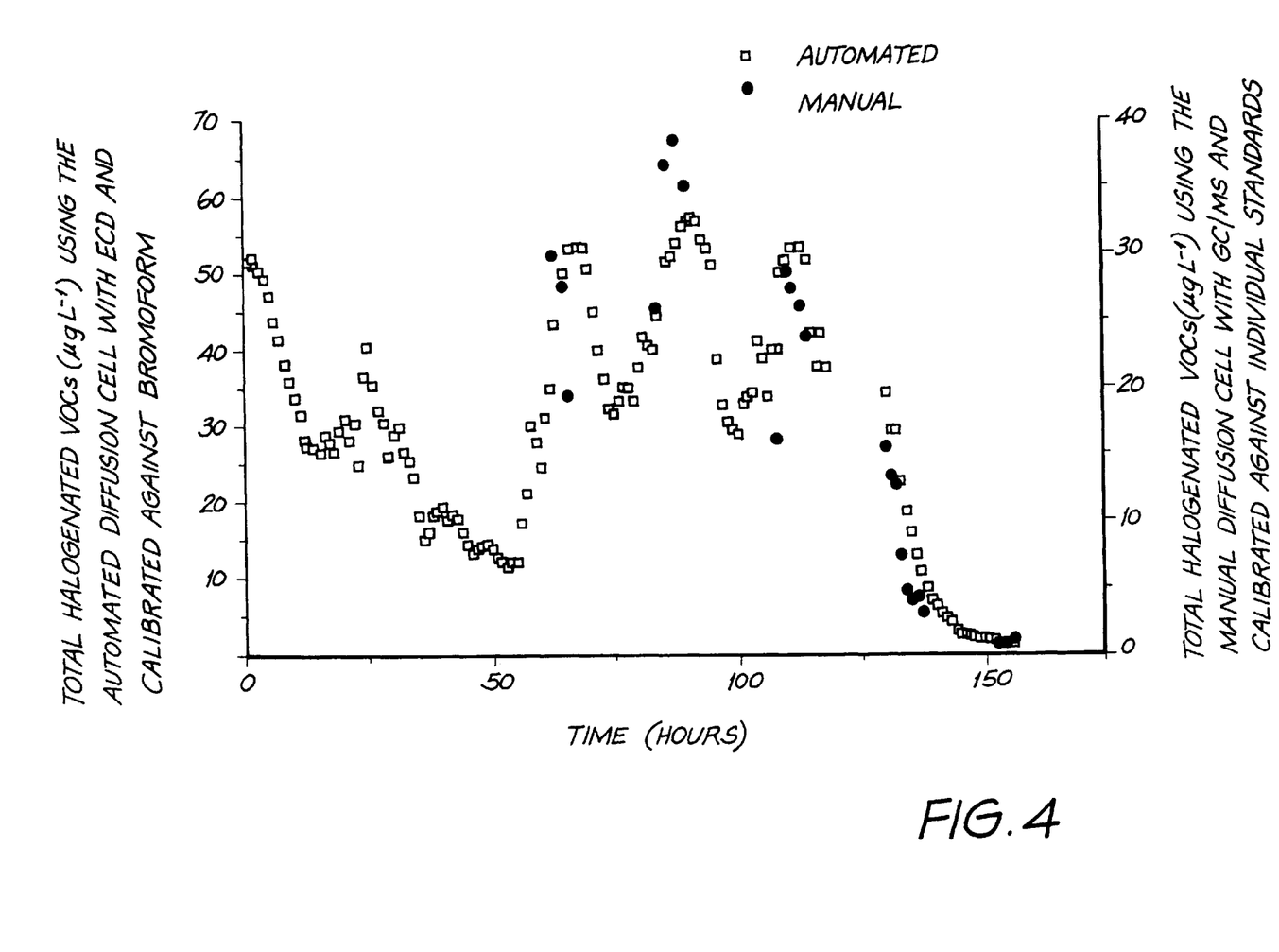
FIG. 4 is a graph showing relative concentrations of halomethanes obtained from the apparatus of FIG. 1 calibrated against bromoform.

The apparatus 10 is used to monitor low level concentrations of VOCs, in this case predominantly halomethanes, in tap water. This is a semi-quantitative measurement since the VOC concentrations are relative to the calibration against TCE or bromform, as shown in FIGS. 3 and 4 respectively. The tap water is continuously passed through the stainless steel flow cell 20 at a nominal flowrate of 100 ml min$^{-1}$. The upstream access line 30 is provided with a continuous flow of pure air 34 at a flowrate of 5 ml min$^{-1}$.

The flow rate of 5 ml min$^{-1}$ is selected to be sufficiently low so that the concentration of VOCs in the diffusion cell 12 is substantially in equilibrium with the concentration of VOCs in the tap water flowing through the flow cell 20. This equilibrium is achieved by using a relatively low flow rate preferably together with a relatively long diffusion cell 12 tube, in this example 1.0 m in length.

The predetermined flow rate will depend on a number of factors including the polymeric material from which the diffusion cell 12 is constructed, the internal and external geometry and dimensions of the diffusion cell, and the composition of the organic compounds in the environmental medium. It is possible to calculate from a mathematical model, based on experimental data relating to the above and other relevant variables, the predetermined flow rate of carrier fluid for any known application.

The predetermined flow rate can be varied to substantially minimise any detrimental response characteristics in respect of certain compounds, such as trimethylbenzene, which have relatively high absorption concentrations within in the diffusion cell 12 compared to compounds such as benzene. The trimethylbenzene partitions significantly more into the diffusion cell 12 compared to benzene. The compounds which have a high degree of partitioning, such as trimethylbenzene, result in a memory effect. The memory effect is such that if the concentration of VOCs changes with time, the concentration of VOCs in the diffusion cell 12 may take a substantial time to equilibrate with the VOC concentration in the environmental medium. This may, therefore, result in an inaccurate detection of VOC concentration until equilibrium is achieved.

An oven 38 is programmed to ramp from 40° C. to 200° C. at a rate of 70° C. per minute (° C. min$^{-1}$). The VOCs that have collected on the carbotrap thermal desorption tube 14 over a period of say 20 minutes or more are then desorbed and an airflow having a concentration of organic compounds is passed for analysis. The logger 42 then records data from the ECD 16.

The results of halomethane gas concentrations relative to TCE and bromoform obtained from the logger 42 over a continuous monitoring period of approximately 5 days are shown in the graphs of FIG. 3 and 4, respectively. The tap water flowing through the flow cell 20 was, at a point corresponding to approximately 125 hours on each of the graphs, changed to a flow of distilled water. As can be seen from both FIGS. 3 and 4 the levels of VOC concentrations recorded by the apparatus 10 gradually fell to substantially zero.

Where the concentration of VOCs, from the carbotrap thermal desorption tube 14 are above the detectable range of the ECD 16, the concentration may need to be lowered prior to analysis. This is achieved by diluting the sample gas from the diffusion cell 12 with a "make-up" gas (not shown). The "make-up" gas can be injected downstream of the desorption tube 14 at a flow rate of, for example, 20 ml/min.

Figure 5:
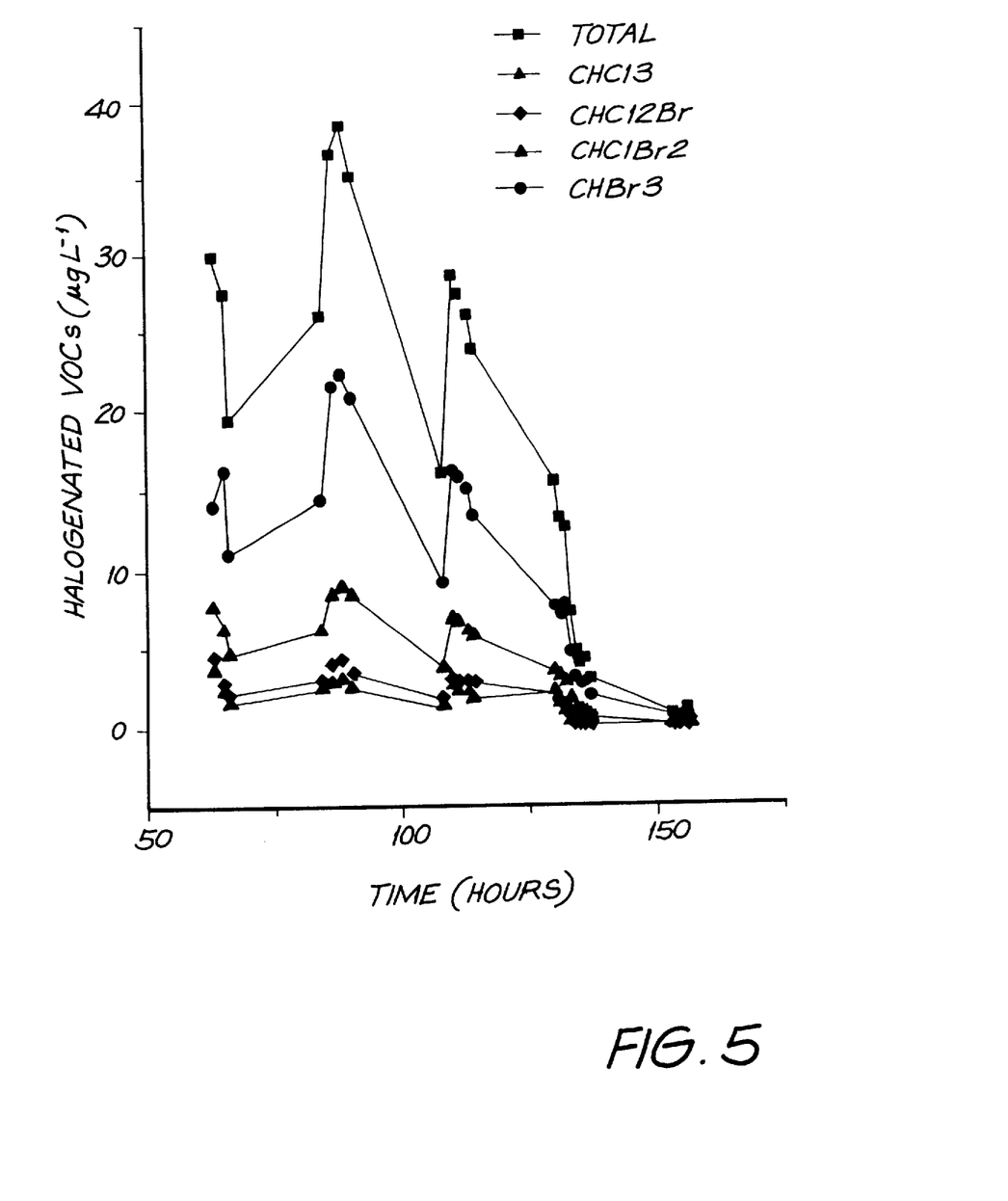
FIG. 5 is a graph showing concentrations of selected halomethanes and total halogenated VOCs in a second diffusion cell analysed with a gas chromatograph/mass spectrometer.

A second diffusion cell (not shown) can also be included in the flow cell 20. Organic samples can be collected manually from this second diffusion cell onto TENAX traps. The organic samples obtained on the TENAX traps can then be thermally desorbed and analysed using a gas chromatograph and a mass spectrometer for detecting individual halomethanes (chloroform, carbontetrachloride, bromodichloromethane, dibromochloromethane, and bromoform). Analytical results obtained from such manually collected samples are shown in the graph of FIG. 5. The plot of total halogenated VOCs is shown in FIG. 4 together with a plot of total halogenated VOCs derived from the apparatus 10. In relative terms the results substantially correspond. A Henry's law constant of 0.045 is used for total halogenated VOCs to determine these relative VOC concentrations.

The sensitivity of a compact solid state detector, in this example a FIGARO Model No. TGS 822 gas sensor can be evaluated using a range of known amounts of, for example, benzene and TCE. A collection period of one hour is used at a carrier fluid flow rate of 5 ml min$^{-1}$. Based on a Henry's law constant for benzene and TCE of 0.24 and 0.36, respectively, detection limits of 20 ng and 90 ng correspond to an aqueous concentration limit of approximately 300 ng $1^{-1}$ and 900 ng $1^{-1}$ respectively.

It has been found that for hydrocarbons the Figaro detector needs oxygen present at greater than 2% to work; this can be achieved using air as the carrier fluid.

Embodiments of the present invention may achieve at least some of the following advantages:

1. The methods described are sensitive to low concentration levels of VOCs in the ppt to ppb range;

2. The apparatus described can provide accurate real-time measurements of VOCs in the ppb range;

3. The apparatus is relatively easy to operate and avoids the steps of sampling and monitoring required in, for example, conventional bore hole or surface water sampling;

4. The apparatus is relatively inexpensive where for instance a compact solid state or similar detector can be used; and, 5. The apparatus allows for continuous environmental monitoring of VOCs, for example, in situ.

It will be apparent to persons skilled in the relevant arts that numerous variations and modifications can be made to the described method and apparatus, in addition to those already mentioned above, without departing from the basic inventive concepts of the present invention. For example the carrier fluid flow rate may be varied according to the dimensions of the diffusion cell so long as the concentration of organic compounds in the environmental medium substantially equilibrate with the concentration of organic compounds within the diffusion cell. The predetermined flow rate can be determined by calibration of a mathematical model based on experimental data. That is, the flow rate and design of a diffusion cell, including polymeric material of construction and tube geometry, can be determined from the experimental data using mathematical models of diffusion and partitioning processes. Alternatively the predetermined flow rate may be calculated by trial and error, using a second diffusion cell together with a gas chromatograph/mass spectrometer as a reference standard for organic compounds contained in the environmental medium.

Furthermore, the apparatus described above could be varied; for example, the concentrating means could be developed using a battery powered heating element, rather than the temperature programmable oven of the gas chromatograph, to desorb organic compounds from the carbotrap desorption tube. The detector may be selected to analyse specific organic compounds from a range of compounds. Advantageously the detector can be a relatively low cost compact solid state device.

The polymeric material for the diffusion cell tube alternatively could be of rubber, PTFE or VITON. Cylindrical cells have also been tested with wall thickness from 0.25 mm to 0.5 mm and outside diameter 1.5 mm to 3 mm.

As shown in the embodiment of FIG. 6 an apparatus for monitoring water comprises a diffusion cell unit 112, 113 and a sample detector unit 138 containing a carbotrap "thermal desorption tube" 114 and a detector in the form of a solid state gas sensor 116. The diffusion cell unit 112 has a stainless steel housing 120 having a water inlet 122 and a water outlet 124.

The diffusion cell unit 112 further comprises a tube 125 of a silicone rubber or other silicone material (such as dimethylsiloxane) shaped in the form of a helical coil. The tube 125, in this example, has an inside diameter of 1.0 mm, an outside diameter of 1.5 mm, and a total length of 1.0 m. The diffusion tube 125 has an upstream end and a downstream end respectively connected to an upstream access line 130 and a downstream access line 132. The upstream access line 130 is connected to at an inlet port 134 to a supply (not shown) of high purity air, which is a carrier fluid supplied to the diffusion cell 12. The downstream access line 132 is connected to the detector unit 138 and incorporates an injection port 136. The injection port 136 of this embodiment is a SWAGELOK T-shaped component.

In this embodiment an absorbent material for absorbing sampled VOCs is contained in the carbotrap thermal desorption tube 114.

The access lines 130 and 132 are of stainless steel which is inert to organic compounds. This avoids the risk of cross-contamination of an organic sample which can occur if the process lines are of a polymeric material.

The apparatus is connected to a power supply 140 and a logger 142 for recording electric signals from the sensor 116 corresponding to concentrations of sample organic compounds by reference to previous calibration, using VOC standards.

Figure 7:
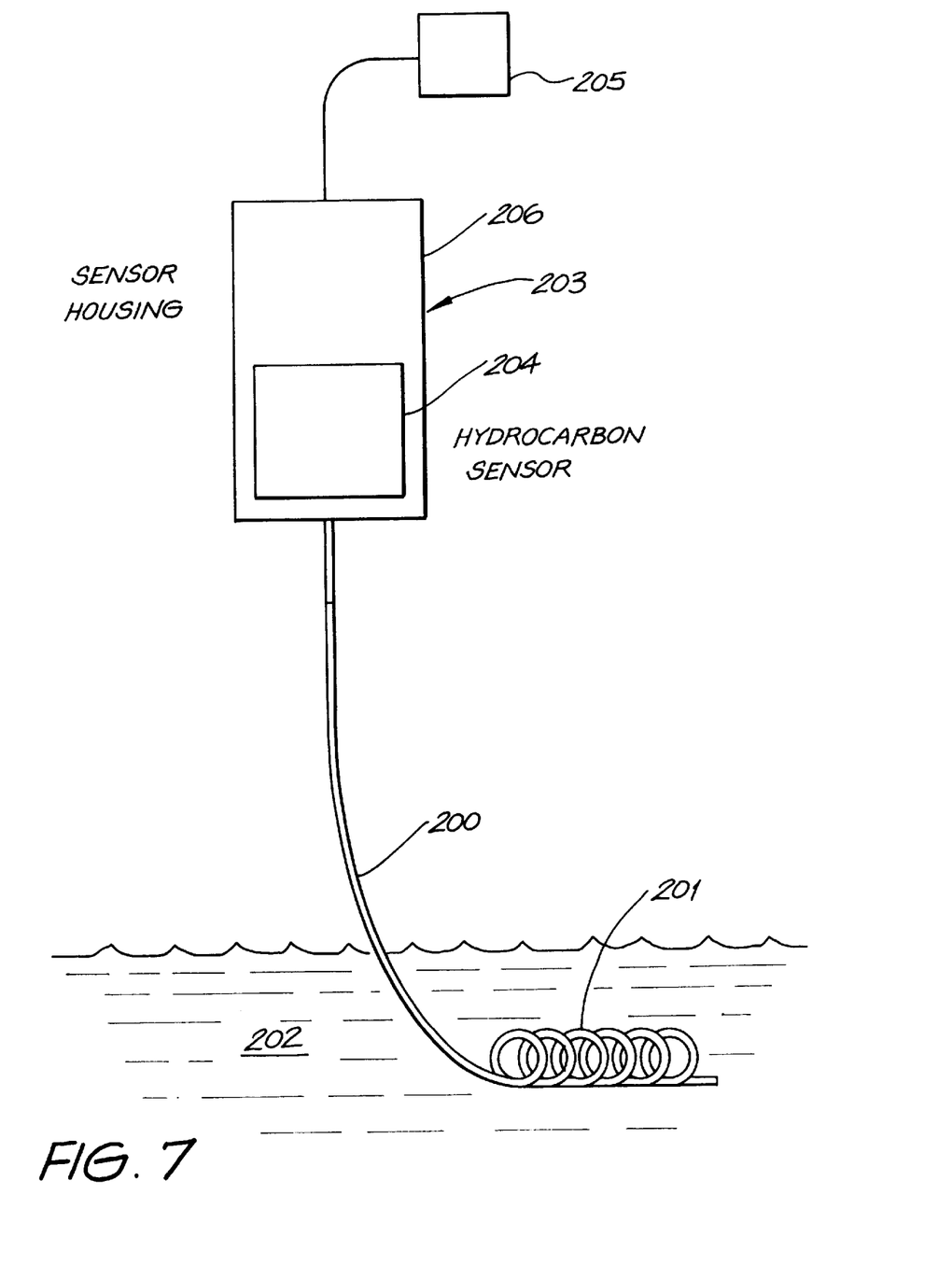
FIG. 7 illustrates schematically a third embodiment wherein there is a close diffusion cell without flow of carrier fluid.

Referring now to FIG. 7 a closed system is provided and consists of a polymeric diffusion cell tube 200 of a silicone material having a helical coil 201 immersed in an environmental fluid where diffusion occurs into and through the wall of the tube by organic compounds in the environmental fluid 202. The tube 200 is connected to a sensor unit 203 having, in this case a low cost commercially available hydrocarbon sensor 204, the unit 203 being connected to a logger 205.

The illustrated embodiment has been found to be suitable for organic fluid detections such as methane, especially where ppm levels are to be detected. Conveniently a Figaro brand sensor is used, models TGS 800, 822, 815 or 842 being suitable. The sensor is sealed within a polycarbonate housing 206 to which is connected the tube 200. In this case the tube has an outside diameter of 3.0 mm, an inside diameter of 2.0 mm, and a wall thickness of 0.5 mm. The Figaro brand sensors contain a heater coil, which heats a sensing element to approximately 400° C.

The sensor could be operated with continuous operation of the sensor heater, but it is advantageous to use intermittent operation for power saving and the reduction of the consumption of methane and production of water vapour within the diffusion cell. This permits the unit to be powered from a 12 volt battery source or a solar panel. Intermittent operation typically will comprise operating the sensor heater for say 200 seconds prior to taking a measurement. The datalogger 205 is used to control both the intermittent logging operation and the preheat time of the sensor, the sensing element being connected in series with a 1180 ohm 0.1% tolerance resistor.

We claim:

1. A method of environmental monitoring of low concentration levels of organic compounds in an environmental medium, the method comprising the steps of:

locating a diffusion cell in the environmental medium for in situ monitoring of the organic compounds, the diffusion cell including a polymeric membrane into which and through which the organic compounds diffuse, providing equilibrium partitioning between the environmental medium, the polymeric membrane and a zone for a carrier fluid, providing flow of the carrier fluid through the zone of the diffusion cell at a relatively low flow rate, the carrier fluid and its flow rate being chosen for the carrier fluid to acquire, before discharge from the zone, a concentration of the organic compounds substantially in equilibrium with the concentration of the organic compounds in the environmental medium and in the polymeric membrane whereby, in use, low concentration levels of the organic compounds in the environmental medium can be detected in a manner which has a relatively high degree of sensitivity, monitoring the organic compounds in the carrier fluid, and providing an output signal representative of the organic compounds in the environmental medium.

2. A method as claimed in claim 1 and including using an equilibrium constant for each organic compound to calculate concentration levels of each of the organic compounds in the environmental medium.

3. A method as claimed in claim 2 and applied to an aqueous environmental medium, the method including using a co-efficient according to Henry's Law to define the equilibrium constant for a plurality of the organic compounds to be detected and controlling the method according to operate under equilibrium partitioning conditions.

4. A method as claimed in any one of the preceding claims and including conducting experiments with known levels of known organic compounds in the environmental medium in order to produce experimental data and effecting calibration using this data whereby a predetermined flow rate of the carrier fluid is selected.

5. A method as claimed in claim 4 and including conducting a preliminary experiment with known organic compounds to determine respective characteristics in terms of different absorbency within the diffusion cell of the organic compounds and determining the predetermined flow rate of the carrier fluid to minimise substantially response characteristics of a memory affect time delay resulting from different levels of absorption of the different organic compounds.

6. A method as claimed in claim 4 and further comprising processing carrier fluid emerging from the diffusion cell and detecting the presence and determining the levels of the organic compounds in the carrier fluid.

7. A method as claimed in claim 6 and including the further step of concentrating the organic compounds in the carrier fluid before the detecting step.

8. A method as claimed in claim 7 and including using a thermal desorption tube to concentrate the organic compounds and using a solid state compact detector to provide real time analysis.

9. A method as claimed in claim 1, wherein the method uses high purity air or nitrogen as the carrier fluid.

10. A method as claimed in claim 9, and wherein the carrier fluid is supplied at a rate of less than 10 ml/min.

11. A method as claimed in claim 1, and including maintaining a closed system for the carrier fluid without flow thereof through the diffusion cell.

12. A method as claimed in claim 6, wherein processing is conducted to monitor one or more organic compounds from the group consisting of benzene, toluene, ethybenzene xylene bromoform, trichloroethene and methane.

13. A method as claimed in claim 1, and operating the method to conduct semi-quantitative real time monitoring of organic compounds.

14. A method as claimed in claim 7, wherein during the concentration step there is utilized a thermal desorption tube, heating means and control means to control absorption by the desorption tube for an extended period of time and then to activate the heating means for a relatively short period of time to cause organic compounds to be desorbed and supplied to a detector for monitoring.

15. An apparatus for use in situ for real-time monitoring of low concentration levels or organic compounds in an environmental medium, the apparatus comprising:

a diffusion cell for sampling the organic compounds in the environmental medium and including a polymeric membrane into which and through which the organic compounds diffuse, the diffusion cell being adapted to provide equilibrium partitioning between the environmental medium, the polymeric membrane and a zone for a carrier fluid, means for controlling flow of the carrier fluid through the zone of the diffusion cell at a relatively low flow rate so that before discharge from the zone, the carrier fluid acquires a concentration of the organic compounds in the environmental medium;

a concentrating means in fluid communication with the diffusion cell for concentrating the sampled organic compounds; and, a detector in fluid communication with the concentrating means for detecting the presence of the organic compounds whereby, in use, low concentration levels of the organic compounds in the environmental medium can be detected with a relatively high degree of sensitivity.

16. An apparatus as claimed in claim 15 and wherein the apparatus further comprises fluid flow generating means coupled to the diffusion cell for generating a predetermined flow rate of a carrier fluid to the diffusion cell and delivering the carrier fluid to the concentrating means.

17. An apparatus as claimed in either claim 15 or 16 and wherein the diffusion cell comprises a tube of silicone material of much greater length than its diameter, the tube being wound into a helical coil, which is immersed in the environmental medium flowing over the exterior of the coil, the tubular helical coil being adapted to conduct the carrier fluid there through.

18. A method of environmental monitoring of low concentration levels of organic compounds in an environmental medium, the method comprising the steps of:

locating a diffusion cell in the environmental medium for sampling the organic compounds, the diffusion cell including a polymeric membrane into which and through which the organic compounds diffuse, the polymeric membrane providing partitioning between the environmental medium and a zone for carrier fluid;

providing the diffusion cell with a carrier fluid such that the carrier fluid acquires a concentration of the organic compounds substantially in equilibrium with the concentration of the organic compounds in the environmental medium whereby, in use, low concentration levels of the organic compounds in the environmental medium can be detected in a manner which has a relatively high degree of sensitivity;

monitoring the organic compounds in the carrier fluid, and providing an output signal representative of the organic compounds in the environmental medium;

conducting experiments with known levels of known organic compounds in the environmental medium in order to produce experimental data and effecting calibration using this data whereby a predetermined flow rate of the carrier fluid is selected; and conducting a preliminary experiment with known organic compounds at known levels in the environmental medium to determine respective characteristics in terms of different absorbency within the diffusion cell of the organic compounds and determining the predetermined flow rate of the carrier fluid to minimise substantially response characteristics of a memory effect time delay resulting from different levels of absorption of the different organic compounds.

19. A method of environmental monitoring of low concentration levels of organic compounds in an environmental medium, the method comprising the steps of:

locating a diffusion cell in the environmental medium for sampling the organic compounds, the diffusion cell including a polymeric membrane into which and through which the organic compounds diffuse, the polymeric membrane providing partitioning between the environmental medium and a zone for carrier fluid;

providing the diffusion cell with a carrier fluid such that the carrier fluid acquires a concentration of the organic compounds substantially in equilibrium with the concentration of the organic compounds in the environmental medium whereby, in use, low concentration levels of the organic compounds in the environmental medium can be detected in a manner which has a relatively high degree of sensitivity; and monitoring the organic compounds in the carrier fluid, and providing an output signal representative of the organic compounds in the environmental medium;

wherein the method uses high purity air or nitrogen as the carrier fluid, the carrier fluid is supplied at a rate of less than 10 ml/min, and wherein the polymeric membrane is an elongate tubular structure.

* * * * *